(12) United States Patent
Maeta et al.

(10) Patent No.: US 10,253,153 B2
(45) Date of Patent: Apr. 9, 2019

(54) LINKER AND SUPPORT FOR SOLID PHASE SYNTHESIS OF NUCLEIC ACID, AND PRODUCTION METHOD OF NUCLEIC ACID USING SAID SUPPORT

(71) Applicant: Nitto Denko Corporation, Ibaraki-shi, Osaka (JP)

(72) Inventors: Eri Maeta, Ibaraki (JP); Kenjiro Mori, Ibaraki (JP); Shohei Horie, Ibaraki (JP); Takahiko Ito, Ibaraki (JP); Shoichiro Saito, Ibaraki (JP); Ryuhei Nagao, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/136,536

(22) Filed: Apr. 22, 2016

(65) Prior Publication Data

US 2016/0311847 A1   Oct. 27, 2016

(30) Foreign Application Priority Data

Apr. 24, 2015   (JP) ................... 2015-089197

(51) Int. Cl.
| | |
|---|---|
| *C07D 493/08* | (2006.01) |
| *C08J 9/36* | (2006.01) |
| *C07H 1/00* | (2006.01) |
| *C07H 21/00* | (2006.01) |

(52) U.S. Cl.
CPC ............ *C08J 9/36* (2013.01); *C07D 493/08* (2013.01); *C07H 1/00* (2013.01); *C07H 21/00* (2013.01); *C07B 2200/11* (2013.01)

(58) Field of Classification Search
USPC ....................................... 549/397
See application file for complete search history.

(56) References Cited

U.S. PATENT DOCUMENTS

| | | | |
|---|---|---|---|
| 5,681,945 A | 10/1997 | McLean et al. | |
| 6,653,468 B1 | 11/2003 | Guzaev et al. | |
| 8,497,376 B2 * | 7/2013 | Illig ................. | C07D 401/14 546/112 |
| 2005/0182241 A1 | 8/2005 | Ngo et al. | |
| 2013/0197117 A1 | 8/2013 | Tsukamoto et al. | |

FOREIGN PATENT DOCUMENTS

| | | | |
|---|---|---|---|
| JP | 2013-177371 A | 9/2013 | |
| WO | WO 2005/049621 A1 | 6/2005 | |
| WO | WO-2009052237 A1 * | 4/2009 | ........... C07D 401/14 |

OTHER PUBLICATIONS

Tetrapropylammonium Perruthenate Catalyzed Glycol Cleavage to Carboxylic (Di)Acids Andrea-Katharina C. Schmid et al, 2011.*
Stereoselective synthesis of highly substituted 8-oxabicyclo[3.2.1]octanes and 2,7-dioxatricyclo[4.2.1.03,8]nonanes Dmitry A. Khlevina, et al , 2012.*
Ghosh et al 2010, Locked Nucleosides based on Oxabicyclo[3.2.1]octane and Oxabicyclo[2.2.1]heptane skeletons.*
Caplus English Abstract DN 155:93671 , 2010 Khlevin D,A. et al (Year: 2010).*
Caplus English Abstract DN 128:230605 , Pham-Huu et al , A nitrohexeneitol 1, 4 addition initiated NEF reaction of D arabinofuranosyl isonitromethanes. (Year: 1997).*
Azhayev et al., "Amide group assisted 3'-dephosphorylation of oligonucleotides synthesized on universal A-supports," *Tetrahedron*, 57: 4977-4986 (2001).
Nelson et al., "Rainbow™ Universal CPG: A Versatile Solid Support for Oligonucleotide Synthesis," *Bio Techniques*, 22(4): 752-756 (Apr. 1997).

(Continued)

*Primary Examiner* — Rita J Desai
(74) *Attorney, Agent, or Firm* — Leydig, Voit & Mayer, Ltd.

(57) ABSTRACT

The present invention provides a linker for solid phase synthesis of nucleic acid, which consists of a compound represented by the formula (I) or the formula (II), a support for solid phase synthesis of nucleic acid, which has a structure represented by the formula (III), and a production method of a nucleic acid, which uses the support:

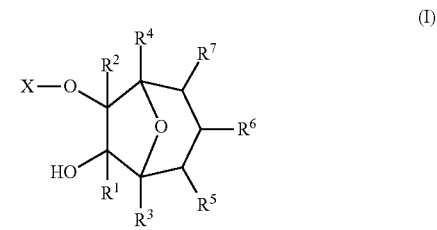

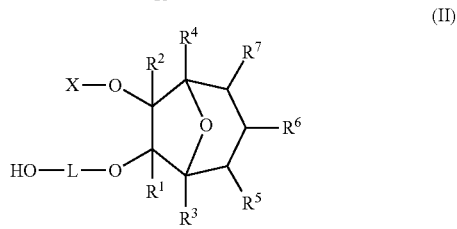

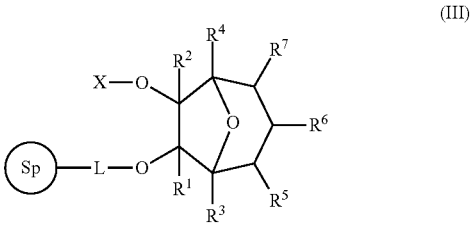

wherein each symbol is as defined in the SPECIFICATION.

11 Claims, 2 Drawing Sheets

Specification includes a Sequence Listing.

(56) References Cited

OTHER PUBLICATIONS

Pon, "Solid-Phase Supports for Oligonucleotide Synthesis," *Current Protocols in Nucleic Acid Chemistry*, 3.1.1-3.128 (2000).

\* cited by examiner

LINKER AND SUPPORT FOR SOLID PHASE SYNTHESIS OF NUCLEIC ACID, AND PRODUCTION METHOD OF NUCLEIC ACID USING SAID SUPPORT

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 826 bytes ASCII (Text) file named "724078SequenceListing.txt," created Apr. 22, 2016.

TECHNICAL FIELD OF THE INVENTION

The present invention relates to a linker to be used for solid phase synthesis of nucleic acid, a support for solid phase synthesis carrying the linker, and a production method of nucleic acid using the support.

BACKGROUND OF THE INVENTION

For chemical synthesis of nucleic acid such as DNA, RNA and the like, a solid phase synthesis process using a phosphoramidite method is widely employed. In the solid phase phosphoramidite method, nucleic acid is generally synthesized by the following steps.

First, nucleoside to be the 3' terminal of the nucleic acid to be synthesized is ester bonded to a cleaving linker such as succinyl group and the like via 3'-OH group so that the nucleoside is previously carried on a support for solid phase synthesis (nucleoside linker). Then, the support for solid phase synthesis on which the nucleoside linker is carried is placed in a reaction column which is then set on an automatic nucleic acid synthesizer.

Thereafter, a synthesis reaction comprising the following steps is generally performed in the reaction column according to a synthesis program of the automatic nucleic acid synthesizer:
(1) a step of deprotection of 5'-OH group of the protected nucleoside with an acid such as trichloroacetic acid/dichloromethane solution and the like;
(2) a step of coupling nucleoside phosphoramidite (nucleic acid monomer) with the deprotected 5'-OH group in the presence of an activator (tetrazole etc.);
(3) a step of capping an unreacted 5'-OH group with acetic anhydride and the like; and
(4) a step of oxidizing phosphite with aqueous iodine and the like.
By repeating the synthesis cycle, an elongation reaction of oligonucleotide from the 3' terminal to the 5' terminal direction is promoted, and a nucleic acid having a desired sequence is synthesized.

Lastly, a cleaving linker is hydrolyzed with aqueous ammonia, methylamine solution and the like to cleave the synthesized nucleic acid from the support for solid phase synthesis (non-patent document 1).

When the above-mentioned synthesis is performed, as mentioned above, it is necessary to carry, in advance, nucleoside to be the 3' terminal (starting material) on a support for solid phase synthesis via a cleaving linker. Moreover, the 3' terminal varies depending on the sequence of nucleic acid desired to be synthesized. In the case of DNA oligonucleotide, 4 kinds of dA, dG, dC, dT are necessary, and in the case of RNA, 4 kinds of rA, rG, rC, rU are also necessary. For synthesis of modified oligonucleotide, a support for solid phase synthesis previously carrying a modified nucleoside is necessary, making the process complicated.

To solve the aforementioned problems, a support for solid phase synthesis carrying a universal linker has been developed as a linker to connect a solid phase support and a starting material, in the place of nucleoside•succinyl linker and the like generally used heretofore. As used herein, the "universal linker" means a linker applicable irrespective of the kind of the 3' terminal nucleoside. In the following, "a support for solid phase synthesis carrying a universal linker" is sometimes described as "universal support". Using the universal support, the process includes, irrespective of the kind of nucleoside or nucleotide for the 3' terminal of nucleic acid desired to be synthesized, reacting nucleoside phosphoramidite to be the 3' terminal in the same step as general automatic nucleic acid synthesis to start the synthesis and, after synthesizing the desired nucleic acid, cleaving the nucleic acid from the support for solid phase synthesis by a method similar to a general method. It is not necessary to prepare a support for solid phase synthesis carrying various nucleoside-linkers as mentioned above.

For example, there are proposed some universal supports, which can synthesize a nucleic acid having a hydroxy group at the 3' terminal (patent documents 1-5 and non-patent documents 2 and 3). The structure of these universal supports has two adjacent carbon atoms, one carbon atom being bound with —OH group to be the starting point of nucleic acid synthesis, and the other carbon atom being bound with a group (e.g., —OH group, —$NH_2$ group, —SH group) to be a nucleophilic group upon removal of the protecting group. When the nucleic acid is cleaved by aqueous ammonia and the like after the nucleic acid synthesis, the protecting group of these nucleophilic groups are also dissociated to attack the 3' terminal phosphorus, and the phosphate group is cleaved from the 3' terminal to form cyclic phosphate. All are used to synthesize nucleic acid having a hydroxy group at the 3' terminal.

Such nucleic acid having a hydroxy group at the 3' terminal is highly useful since it is widely demanded in the biochemical field, such as a nucleic acid drug and the like.

However, conventionally-known methods using a universal support do not show a sufficient synthesis efficiency of DNA or RNA.

In view of such situation, a universal linker capable of inhibiting generation of byproducts and capable of synthesizing DNA or RNA more efficiently at a high purity, as well as a support for solid phase synthesis of nucleic acid which carries the linker have been demanded.

DOCUMENT LIST

Patent Documents

[patent document 1] U.S. Pat. No. 5,681,945
[patent document 2] U.S. Pat. No. 6,653,468
[patent document 3] WO 2005/049621
[patent document 4] US 2005/0182241 A1
[patent document 5] JP-A-2013-177371

Non-Patent Documents

[non-patent document 1] Current Protocols in Nucleic Acid Chemistry (2000) 3.1.1-3.1.28
[non-patent document 2] Bio Techniques, 22, 752-756 (1997)
[non-patent document 3] Tetrahedron, 57, 4977-4986 (2001)

SUMMARY OF THE INVENTION

Problems to be Solved by the Invention

The present invention aims to provide a universal linker capable of inhibiting generation of byproducts and capable of synthesizing DNA or RNA more efficiently at a high purity, a support for solid phase synthesis of nucleic acid which carries the linker, and a production method of a nucleic acid, which uses the support.

Means of Solving the Problems

Therefore, the present invention provides the following.

[1] A linker for solid phase synthesis of nucleic acid, consisting of a compound represented by the formula (I):

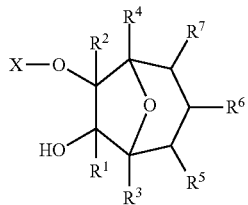

(I)

wherein

X is a hydrogen atom, or a hydroxy-protecting group which is cleaved with an acid; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by substituent(s) selected from a cyano group and a phenyl group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

[2] A linker for solid phase synthesis of nucleic acid, consisting of a compound represented by the formula (II):

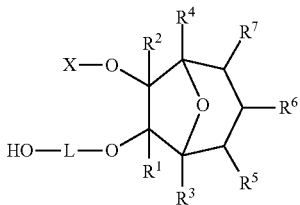

(II)

wherein

X is a hydrogen atom, or a hydroxy-protecting group which is cleaved with an acid;

L is a linking part which is cleaved by an alkali; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by substituent(s) selected from a cyano group and a phenyl group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

[3] The linker for solid phase synthesis of nucleic acid of the above-mentioned [2], wherein L is a divalent group represented by the formula (L):

(L)

wherein $L^1$ is an inactive divalent group; and * and ** each show a binding site.

[4] The linker for solid phase synthesis of nucleic acid of any of the above-mentioned [1]-[3], wherein X is a hydroxy-protecting group which is cleaved with an acid.

[5] The linker for solid phase synthesis of nucleic acid of any of the above-mentioned [1]-[4], wherein the hydroxy-protecting group which is cleaved with an acid is a trityl protecting group or a silyl protecting group.

[6] A support for solid phase synthesis of nucleic acid, having a structure shown by the formula (III):

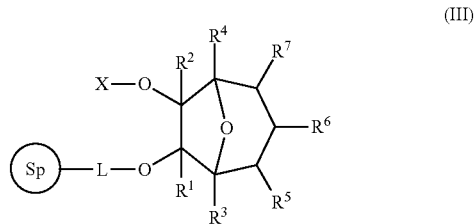

(III)

wherein

X is a hydrogen atom, or a hydroxy-protecting group which is cleaved with an acid;

L is a linking part which is cleaved by an alkali;

Sp is a solid phase support; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by substituent(s) selected from a cyano group and a phenyl group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

[7] The support for solid phase synthesis of nucleic acid of the above-mentioned [6], wherein L is a divalent group represented by the formula (L):

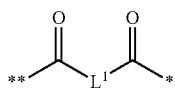

wherein L¹ is an inactive divalent group; and * and ** each show a binding site.

[8] The support for solid phase synthesis of nucleic acid of the above-mentioned [6] or [7], wherein X is a hydroxy-protecting group which is cleaved with an acid.

[9] The support for solid phase synthesis of nucleic acid of any of the above-mentioned [6]-[8], wherein the hydroxy-protecting group which is cleaved with an acid is a trityl protecting group or a silyl protecting group.

[10] The support for solid phase synthesis of nucleic acid of any of the above-mentioned [6]-[9], wherein the bond between Sp and L is an amide bond or an ester bond.

[11] The support for solid phase synthesis of nucleic acid of any of the above-mentioned [6]-[10], wherein Sp is a solid phase support of a porous polymer support or a porous glass support.

[12] A method of producing a nucleic acid, comprising a step of performing a nucleic acid synthesis reaction on the support for solid phase synthesis of nucleic acid according to any of the above-mentioned [6]-[11].

[13] The production method of the above-mentioned [12], wherein the nucleic acid synthesis reaction is performed by a solid phase phosphoramidite method.

Effect of the Invention

The support for solid phase synthesis of nucleic acid of the present invention can inhibit generation of byproducts and can synthesize DNA or RNA more efficiently at a high purity.

DESCRIPTION OF EMBODIMENTS

Figure 1:
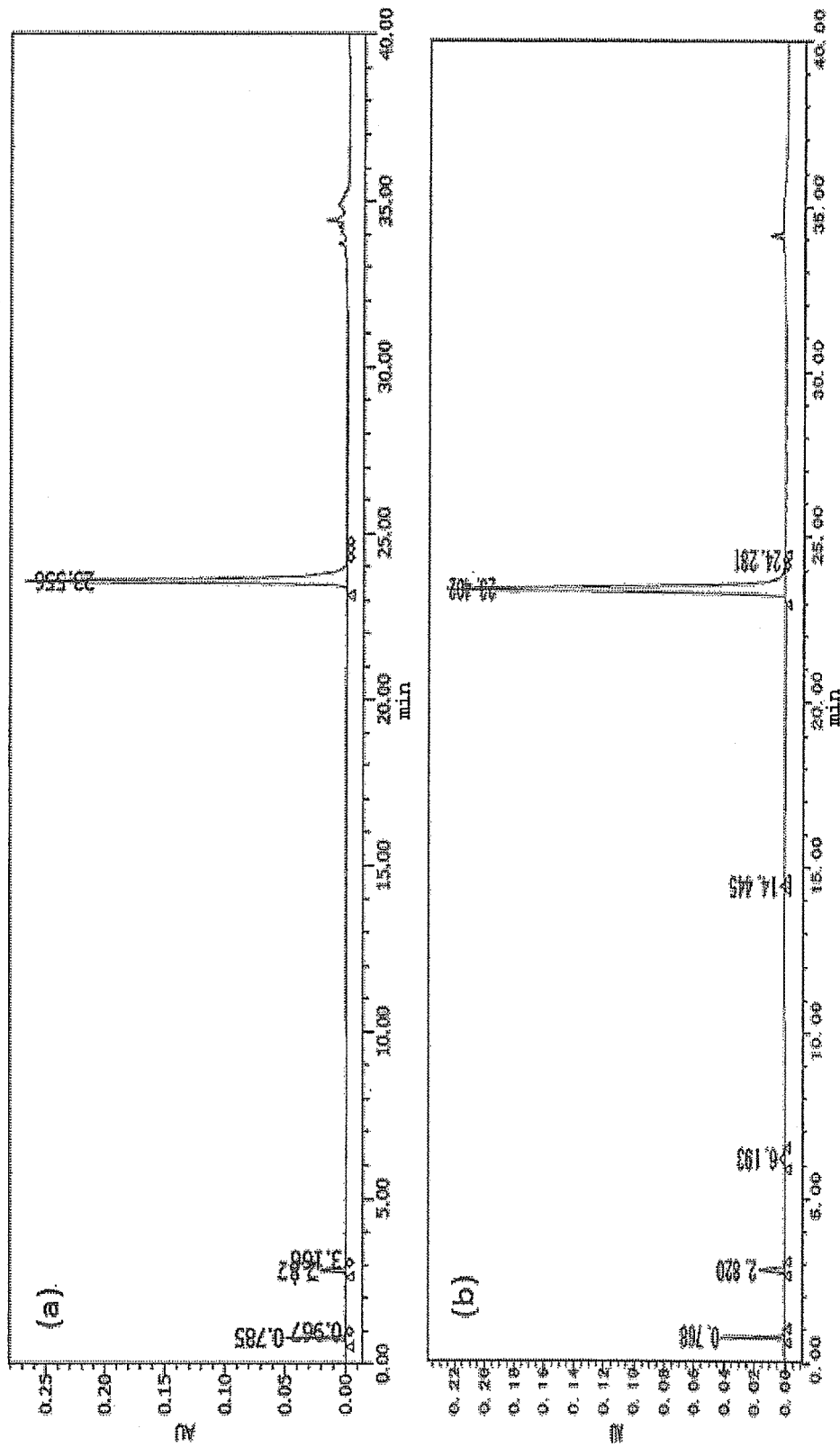
FIG. 1 shows HPLC charts of the DNA oligonucleotide solutions obtained in Example 1 (FIG. 1(a)) and Comparative Example 1 (FIG. 1(b)).

The present invention provides a linker for solid phase synthesis of nucleic acid, which consists of a compound represented by the following formula (I):

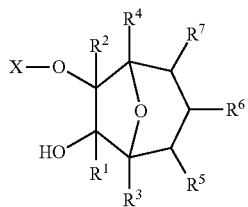

wherein
X is a hydrogen atom, or a hydroxy-protecting group which is cleaved with an acid; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by substituent(s) selected from a cyano group and a phenyl group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

In the present specification, examples of the "$C_{1-6}$ alkyl group" include methyl group, ethyl group, n-propyl group, isopropyl group, n-butyl group, isobutyl group, sec-butyl group, tert-butyl group, n-pentyl group, isopentyl group, sec-pentyl group, tert-pentyl group, hexyl group and the like. Of these, methyl group or ethyl group is preferable.

In the present specification, examples of the "carbamoyl group optionally mono- or di-substituted by substituent(s) selected from a $C_{1-6}$ alkyl group and a phenyl group" include carbamoyl group, methylcarbamoyl group, ethylcarbamoyl group, n-propylcarbamoyl group, isopropylcarbamoyl group, n-butylcarbamoyl group, isobutylcarbamoyl group, sec-butylcarbamoyl group, tert-butylcarbamoyl group, n-pentylcarbamoyl group, isopentylcarbamoyl group, sec-pentylcarbamoyl group, tert-pentylcarbamoyl group, hexylcarbamoyl group, dimethylcarbamoyl group, diethylcarbamoyl group, di-n-propylcarbamoyl group, di-isopropylcarbamoyl group, di-n-butylcarbamoyl group, di-isobutylcarbamoyl group, di-sec-butylcarbamoyl group, di-tert-butylcarbamoyl group, di-n-pentylcarbamoyl group, di-isopentylcarbamoyl group, di-sec-pentylcarbamoyl group, di-tert-pentylcarbamoyl group, dihexylcarbamoyl group, N-methyl-N-ethylcarbamoyl group, phenylcarbamoyl group, diphenylcarbamoyl group, N-methyl-N-phenylcarbamoyl group and the like. Of these, carbamoyl group, methylcarbamoyl group, ethylcarbamoyl group or phenylcarbamoyl group is preferable.

In the present specification, examples of the "$C_{1-6}$ alkoxy group" include methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, tert-pentyloxy group, hexyloxy group and the like. Of these, methoxy group or ethoxy group is preferable.

In the present specification, examples of the "$C_{1-6}$ alkyl group optionally substituted by a $C_{1-6}$ alkoxy group" include those exemplified for the above-mentioned "$C_{1-6}$ alkyl group", and methoxymethyl group, methoxyethyl group, methoxy-n-propyl group, methoxyisopropyl group, ethoxymethyl group, n-propoxymethyl group, n-butoxymethyl group and the like. Of these, methyl group, ethyl group, methoxymethyl group or methoxyethyl group is preferable.

In the present specification, examples of the "halogen atom" include chlorine atom, fluorine atom, bromine atom, and iodine atom. Of these, chlorine atom, fluorine atom or bromine atom is preferable.

In the present specification, examples of the "phenyl group optionally substituted by substituent(s) selected from a $C_{1-6}$ alkoxy group, a $C_{1-6}$ alkyl group, a nitro group, and a halogen atom" include phenyl group, phenyl group substituted by $C_{1-6}$ alkoxy group, phenyl group substituted by $C_{1-6}$ alkyl group, phenyl group substituted by halogen atom, phenyl group substituted by nitro group (each described in detail in the following) and the like.

In the present specification, examples of the "phenyl group substituted by $C_{1-6}$ alkoxy group" include methoxyphenyl group, ethoxyphenyl group, n-propylphenyloxy group, isopropyloxyphenyl group, n-butyloxyphenyl group, isobutyloxyphenyl group, tert-butyloxyphenyl group, dimethoxyphenyl group and the like. Of these, methoxyphenyl group, benzylethyletherethoxyphenyl group, tert-butyloxyphenyl group or dimethoxyphenyl group is preferable.

In the present specification, examples of the "phenyl group substituted by $C_{1-6}$ alkyl group" include methylphenyl group, ethylphenyl group, n-propylphenyl group, isopropylphenyl group, n-butylphenyl group, isobutylphenyl group, tert-butylphenyl group, dimethylphenyl group and the like. Of these, methylphenyl group, tert-butylphenyl group or dimethylphenyl group is preferable.

In the present specification, examples of the "phenyl group substituted by halogen atom" include chlorinated phenyl group, fluorinated phenyl group, brominated phenyl group, dichlorinated phenyl group, difluorinated phenyl group, dibrominated phenyl group and the like. Of these, fluorinated phenyl group, brominated phenyl group or dibrominated phenyl group is preferable.

In the present specification, examples of the "phenyl group substituted by nitro group" include 2-nitrophenyl group, 3-nitrophenyl group, 4-nitrophenyl group, 2,4-dinitrophenyl group and the like. Of these, 4-nitrophenyl group is preferable.

In the present specification, examples of the "$C_{1-7}$ acyl" moiety in the "$C_{1-7}$ acyl group" and "$C_{1-7}$ acylamino group" include (1) formyl group, (2) carboxy group, (3) $C_{1-6}$ alkyl-carbonyl group, (4) $C_{1-6}$ alkoxy-carbonyl group, (5) benzoyl group and the like.

Examples of the "$C_{1-6}$ alkyl-carbonyl group" include acetyl group, propanoyl group, butanoyl group, isobutanoyl group, pentanoyl group, isopentanoyl group, hexanoyl group and the like. Of these, acetyl group is preferable.

Examples of the "$C_{1-6}$ alkoxy-carbonyl group" include methoxycarbonyl group, ethoxycarbonyl group, n-propoxycarbonyl group, isopropoxycarbonyl group, n-butoxycarbonyl group, n-pentyloxycarbonyl group, isopentyloxycarbonyl group, sec-pentyloxycarbonyl group, tert-pentyloxycarbonyl group, hexyloxycarbonyl group and the like. Of these, methoxycarbonyl group is preferable.

Of the above-mentioned "$C_{1-7}$ acyl groups", $C_{1-6}$ alkyl-carbonyl group, benzoyl group and the like are preferable, and acetyl group and benzoyl group are particularly preferable.

In the present specification, examples of the "$C_{1-7}$ acylamino group" include formylamino group, acetylamino group, propanoylamino group, butanoylamino group, isobutanoylamino group, pentanoylamino group, isopentanoylamino group, hexanoylamino group, methoxycarbonylamino group, ethoxycarbonylamino group, n-propoxycarbonylamino group, isopropoxycarbonylamino group, n-butoxycarbonylamino group, n-pentyloxycarbonylamino group, isopentyloxycarbonylamino group, sec-pentyloxycarbonylamino group, tert-pentyloxycarbonylamino group, hexyloxycarbonylamino group, benzoylamino group and the like. Of these, acetylamino group or benzoylamino group is preferable.

In the present specification, examples of the "$C_{1-6}$ alkoxy group optionally substituted by substituent(s) selected from a cyano group and a phenyl group" include those exemplified as the above-mentioned "$C_{1-6}$ alkoxy group", cyanomethoxy group, benzyloxy group and the like.

In the present specification, examples of the "mono or di-$C_{1-6}$ alkylamino group" include methylamino group, ethylamino group, n-propylamino group, isopropylamino group, n-butylamino group, isobutylamino group, sec-butylamino group, tert-butylamino group, n-pentylamino group, isopentylamino group, sec-pentylamino group, tert-pentylamino group, hexylamino group, dimethylamino group, diethylamino group, di-n-propylamino group, diisopropylamino group, di-n-butylamino group and the like. Of these, methylamino group, dimethylamino group, ethylamino group, diethylamino group is preferable, particularly methylamino group or dimethylamino group is preferable.

In the present specification, examples of the "mono or di-phenylamino group" include phenylamino group and diphenylamino group. Of these, phenylamino group is preferable.

In the present specification, "optionally substituted" means an embodiment including being unsubstituted or being substituted by 1 to 3 substituents. In the case of 2 or 3 substitutions, respective substituents may be the same or different.

In the present specification, "substituted" means an embodiment including being substituted by 1 to 3 substituents. In the case of 2 or 3 substitutions, respective substituents may be the same or different.

In a preferable embodiment, X is a hydroxy-protecting group which is cleaved with an acid.

While the hydroxy-protecting group which is cleaved with an acid is not limited as long as it is a protecting group permitting deprotection with a Broensted acid such as trichloroacetic acid, dichloroacetic acid and the like, and examples thereof include trityl protecting group, silyl protecting group and the like.

In the present specification, examples of the "trityl protecting group" include trityl group optionally substituted by any substituent (e.g., substituent selected from $C_{1-6}$ alkoxy group, $C_{1-6}$ alkyl group, halogen atom and the like (two or more substituents may be joined to form a ring)), specifically, trityl group (Tr), monomethoxytrityl group (e.g., 4-methoxytrityl group (MMTr)), dimethoxytrityl group (e.g., 4,4'-dimethoxytrityl group (DMTr)), 9-phenylxanthen-9-yl group (pixyl group) and the like. Preferred is 4,4'-dimethoxytrityl group (DMTr).

In the present specification, examples of the "silyl protecting group" include silyl group trisubstituted by any substituent (e.g., substituent selected from $C_{1-6}$ alkoxy group, $C_{1-6}$ alkyl group, phenyl group and the like), specifically, trimethylsilyl group, triethylsilyl group, isopropyldimethylsilyl group, tert-butyldimethylsilyl group, dimethylmethoxysilyl group, methyldimethoxysilyl group, tert-butyldiphenylsilyl group and the like. Preferred is trimethylsilyl group.

Since the hydroxy-protecting group which is cleaved with an acid is preferably a trityl protecting group, more preferably a 4,4'-dimethoxytrityl group (DMTr), since it is easily deprotected by an acid.

$R^1$-$R^4$ are preferably hydrogen atoms.

$R^5$-$R^7$ are preferably each independently (1) a hydrogen atom; (2) a cyano group; (3) a nitro group; (4) a carbamoyl group optionally mono- or di-substituted by substituent(s) selected from a $C_{1-6}$ alkyl group and a phenyl group (e.g., carbamoyl group, methylcarbamoyl group, phenylcarbamoyl group); (7) a $C_{1-6}$ alkoxy group optionally substituted by substituent(s) selected from a cyano group and a phenyl group (e.g., methoxy group, ethoxy group, benzyloxy group, cyanomethoxy group); (8) a phenoxy group; (9) a $C_{1-7}$ acyl group (e.g., acetyl group, benzoyl group); (10) a mono- or di-$C_{1-6}$ alkylamino group (e.g., methylamino group, dimethylamino group); (11) a mono- or di-phenylamino group (e.g., phenylamino group); (12) a $C_{1-7}$ acylamino group (e.g., acetylamino group, benzoylamino group); or (13) a halogen atom (e.g., chlorine atom, bromine atom).

$R^5$ and $R^7$ are more preferably hydrogen atoms.

$R^6$ is more preferably a carbamoyl group optionally mono- or di-substituted by substituent(s) selected from $C_{1-6}$ alkyl group and phenyl group, further preferably a carbamoyl group, a methylcarbamoyl group or a phenylcarbamoyl group, particularly preferably a methylcarbamoyl group.

The compound represented by the formula (I) (linker for solid phase synthesis of nucleic acid) is a linker for connecting a reactant (i.e., nucleic acid) and a support in solid phase synthesis, and can be used as a starting material for forming a synthesis initiation site of a support for solid phase synthesis of nucleic acid (i.e., structure represented by the formula (LIII) that binds to the below-mentioned solid phase support for Sp). As used herein, the synthesis initiation site is a part to which a reactant is first bonded chemically in an elongation reaction for solid phase synthesis.

The present invention also provides a linker for solid phase synthesis of nucleic acid, which consists of a compound represented by the following formula (II).

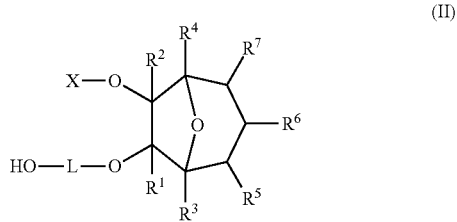

wherein L is a linking part which is cleaved by an alkali; and other symbols are as defined above.

L is not particularly limited as long as it is a structure permitting cleavage of the covalent bond between L and O by treating with an alkali such as ammonia and/or amines and the like and is, for example, a divalent group represented by the formula (L):

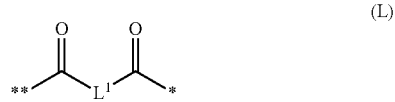

wherein $L^1$ is an inactive divalent group; and * and ** each show a binding site.

In the present specification, "inactive" of the "inactive divalent group" means that it does not have a functional group that inhibits a solid phase synthesis reaction of hydroxy group, amino group, carboxy group, sulfanyl group, sulfo group and the like.

$L^1$ is preferably an inactive divalent group having a main chain composed of atom(s) (preferably 1-200, more preferably 1-25, further preferably 1-10) selected from carbon atom, oxygen atom, sulfur atom and nitrogen atom.

$L^1$ is more preferably a divalent group represented by the formula: —[(CR$_2$)$_a$-A-]$_b$-(CR$_2$)$_c$— wherein A is a bond, —O—, —S—, —SO$_2$—, —CO—, -Ph-, —OPhO—, —CONH—, —NHCO— and the like; each R is independently a hydrogen atom, a $C_{1-6}$ alkyl group, a $C_{1-6}$ alkoxy group, a $C_{1-6}$ alkylthio group and the like; a and c are each independently an integer of 1-6 (preferably 1-3), and b is an integer of 0-6 (preferably 0-3)].

In the present specification, examples of the "$C_{1-6}$ alkylthio group" include methylthio group, ethylthio group, propylthio group, butylthio group, pentylthio group, and hexylthio group.

$L^1$ is further preferably —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$OCH$_2$—, —CH$_2$CH$_2$OCH$_2$CH$_2$—, —CH$_2$CH$_2$OCH$_2$CH$_2$CH$_2$—, —CH$_2$CH$_2$OCH$_2$CH$_2$OCH$_2$CH$_2$—, —CH$_2$SCH$_2$—, —CH$_2$CH$_2$SCH$_2$CH$_2$—, —CH$_2$CH$_2$CH$_2$SCH$_2$CH$_2$CH$_2$—, —CH$_2$CH$_2$SCH$_2$CH$_2$SCH$_2$CH$_2$—, —CH$_2$SO$_2$CH$_2$—, —CH$_2$CH$_2$SO$_2$CH$_2$CH$_2$—, —CH$_2$CH$_2$CH$_2$SO$_2$CH$_2$CH$_2$CH$_2$—, —CH$_2$CH$_2$SO$_2$CH$_2$CH$_2$SO$_2$CH$_2$CH$_2$—, —CH$_2$COCH$_2$—, —CH$_2$CH$_2$COCH$_2$CH$_2$—, —CH$_2$CH$_2$CH$_2$COCH$_2$CH$_2$CH$_2$—, —CH$_2$CH$_2$COCH$_2$CH$_2$COCH$_2$CH$_2$—, -Ph-, —CH$_2$PhCH$_2$—, —CH$_2$CH$_2$PhCH$_2$CH$_2$—, —CH$_2$CH$_2$CH$_2$PhCH$_2$CH$_2$CH$_2$—, —CH$_2$CH$_2$PhCH$_2$CH$_2$PhCH$_2$CH$_2$—, —CH$_2$OPhOCH$_2$—, —CH$_2$CH$_2$OPhOCH$_2$CH$_2$—, —CH$_2$CH$_2$CH$_2$OPhOCH$_2$CH$_2$CH$_2$—, —CH$_2$CH$_2$OPhOCH$_2$CH$_2$OPhOCH$_2$CH$_2$— or the like.

$L^1$ is particularly preferably —CH$_2$CH$_2$—. L is particularly preferably a succinyl group.

The above-mentioned "Ph" is 1,4-phenylene, 1,3-phenylene or 1,2-phenylene.

The compound represented by the formula (II) (linker for solid phase synthesis of nucleic acid) is a linker for connecting a reactant (i.e., nucleic acid) and a support in solid phase synthesis, and can be used as a starting material for forming a synthesis initiation site of a support for solid phase synthesis of nucleic acid (i.e., structure represented by the formula (LIII) that binds to the below-mentioned solid phase support for Sp). As used herein, the synthesis initiation site is a part to which a reactant is first bonded chemically in an elongation reaction for solid phase synthesis. In the solid phase synthesis, the moiety represented by HO-L- in the formula (II) is chemically bonded to a solid phase support in advance, and a reactant is chemically bonded to a hydroxy group obtained by deprotecting the protecting group represented by X to repeat the chemical reaction, whereby the nucleic acid can be elongated.

The compound represented by the formula (II) also encompasses a salt form. Examples of the salt include alkali metal salts (e.g., sodium salt, potassium salt), alkaline earth metal salts (e.g., calcium salt) and the like.

In addition, the present invention provides support for solid phase synthesis of nucleic acid represented by the following formula (III) (universal support):

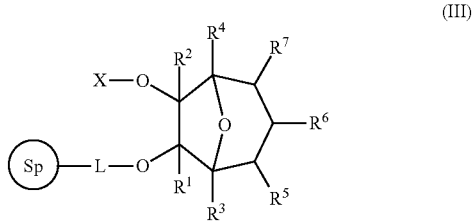

wherein Sp shows a solid phase support; and other symbols are as defined above.

In the present specification, "nucleic acid" refers to a linear compound (oligonucleotide) wherein nucleotides are connected via phosphodiester bonds, and is understood to encompass DNA, RNA and the like. The nucleic acid may be single-stranded or double-stranded. Since it allows an efficient synthesis using a nucleic acid synthesizer, the nucleic acid is preferably single-stranded. The "nucleic acid" in the present specification includes not only an oligonucleotide containing a purine base such as adenine (A), guanine (G) and a pyrimidine base such as thymine (T), cytosine (C), uracil (U) but also a modified oligonucleotide containing a modified nucleic acid base thereof.

The solid phase support for Sp is not particularly limited as long as it is a support for solid phase synthesis in which a reagent used in excess can be easily removed by washing and, for example, porous glass support, porous synthetic polymer support such as porous polystyrene support, porous acrylamide support and the like can be mentioned. Preferred are porous polystyrene support and porous glass support, and more preferred is porous polystyrene support.

In the present specification, the "porous glass support" refers to a porous support containing glass as a constituent component and examples thereof include, but are not limited to, porous glass particles in a granular shape (CPG) and the like. More specifically, as the aforementioned CPG, a CPG solid phase support having a long chain aminoalkyl spacer (LCAA-CPG solid phase support) is preferably used, and further, for the synthesis of a long chain nucleotide, one having a CPG pore of preferably 20-400 nm, more preferably 50-200 nm, most preferably 100 nm, is used.

In the present specification, the "porous polystyrene support" is a porous support mainly composed of a resin constituted of a structural unit of styrene or a derivative thereof and, among others, a porous polystyrene support having an amino group and/or a hydroxy group is preferable.

Examples of the porous polystyrene support include a porous support composed of styrene-hydroxystyrene-divinylbenzene copolymer particles (see JP-A-2005-097545, JP-A-2005-325272 and JP-A-2006-342245), a porous support composed of a styrene-(meth)acrylonitrile-hydroxystyrene-divinylbenzene copolymer (see JP-A-2008-074979) and the like.

In the present specification, the "porous acrylamide support" is a porous support mainly composed of a resin constituted of a structural unit of acrylamide or a derivative thereof and, among others, a porous acrylamide support having an amino group and/or a hydroxy group is preferable, and a porous acrylamide support having a hydroxy group is preferable.

Examples of the porous acrylamide support include one composed of an aromatic monovinyl compound-divinyl compound-(meth)acrylamide derivative copolymer and the like. When Sp is an acrylamide solid phase support and the content of the structural unit derived from a (meth)acrylamide derivative monomer is too small, an effect of obviating a decrease in the synthesis amount of the nucleic acid and lower synthesis purity cannot be afforded; on the other hand, when it is too high, porous resin beads are difficult to form. Accordingly, it is preferably 0.3-4 mmol/g, more preferably 0.4-3.5 mmol/g, further preferably 0.6-3 mmol/g.

In the present invention, the solid phase support may be any solid phase support having a functional group capable of introducing a structure represented by the formula (LIII):

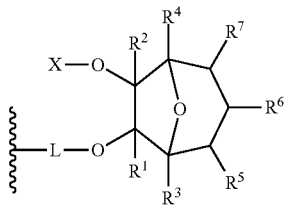

(LIII)

wherein each symbol is as defined above. It is preferably a solid phase support having an amino group and/or a hydroxy group (particularly preferably, a hydroxy group). In this case, the bond between Sp and L is, for example, an amide bond or an ester bond (preferably, an ester bond).

The content of the functional group that can introduce the structure represented by the formula (LIII) in the solid phase support of the present invention is not particularly limited. When the content of the functional group is too small, the yield of nucleic acid decreases and when it is too high, the purity of the obtained nucleic acid decreases. Therefore, it is preferably 10-2000 μmol/g, more preferably 50-1000 μmol/g, further preferably 100-800 μmol/g.

When the functional group that can introduce the structure represented by the formula (LIII) is a hydroxyl group, the amount of the hydroxyl group of the porous particles of the present invention is measured by titration based on JIS K0070.

In the present invention, the shape of the solid phase support is not particularly limited and may be any shape of plate, particle, fiber and the like. Since the packing efficiency to a synthesis reaction container can be enhanced, and the reaction container is not easily broken, a porous polymer having a particle shape is preferable. The term "particle" in the specification does not mean being exactly spherical, but means having any constant form (e.g., roughly spherical forms such as ellipse spherical, polygonal form, cylindrical form, irregular forms such as konpeito form, and the like).

In the present invention, while the size (volume) of the solid phase support is not particularly limited, when the average particle size measured by laser diffraction (scattering type) of the porous particles is smaller than 1 μm, inconvenience occurs when it is packed in a column and used in that the back pressure becomes too high or a solution sending rate becomes slow. On the other hand, when the average particle size is more than 1000 μm, the gap between the support particles becomes large and efficient packing of support particles in a column having a predetermined volume becomes difficult. Therefore, it is preferably 1-1000 μm, more preferably 5-500 μm, further preferably 10-200 μm.

In the present invention, while the specific surface area of the solid phase support as measured by a multi-point BET method is not particularly limited, when the specific surface area is less than 0.1 m$^2$/g, the degree of swelling in an organic solvent becomes low, and a synthesis reaction tends to be difficult to occur. On the other hand, when it is more than 500 m$^2$/g, pore size becomes small, and a synthesis reaction tends to be difficult to occur. Therefore, the specific surface area is preferably 0.1-500 m$^2$/g, more preferably 10-300 m$^2$/g, further preferably 50-200 m$^2$/g.

In the present invention, the average pore size of the solid phase support as measured by a mercury intrusion technique is not particularly limited. However, when the pore size is too small, the field of the synthesis reaction becomes small and a desired reaction does not occur easily, or the nucleotide length tends to be less than a desired number. On the other hand, when the pore size is too large, the frequency of contact between a hydroxyl group and a substance involved in the reaction on the surface of polymer particles, which is the reaction field, decreases to lower the yield. Therefore the average pore size is preferably 1-200 nm, more preferably 5-100 nm, more preferably 20-70 nm.

In the present invention, the solid phase support is particularly preferably a low swelling crosslinked polystyrene particle commercially available as NittoPhase (registered trade mark) (manufactured by NITTO DENKO Co., Ltd.). A solid phase nucleic acid synthesis method using NittoPhase (registered trade mark) is preferably used since it shows a small peak area due to impurity and guarantees high yield and high purity in a wide scale from labo scale to mass synthesis system.

In the support for solid phase synthesis of nucleic acid, which is represented by the formula (III), the forming amount of a structure represented by the formula (LIII), which is bonded to a solid phase support for Sp (binding amount of universal linker) is not particularly limited. When the binding amount of the linker is too low, the yield of nucleic acid decreases. Therefore, it is preferably not less than 45 µmol/g, more preferably, not less than 50 µmol/g.

The amount of the linker bonded to the solid phase support can be measured by a known method and using a spectrophotometer.

While the production method of the support for solid phase synthesis of nucleic acid of the present invention is not particularly limited, for example, the support can be produced by the following scheme 1 (steps 1-4).

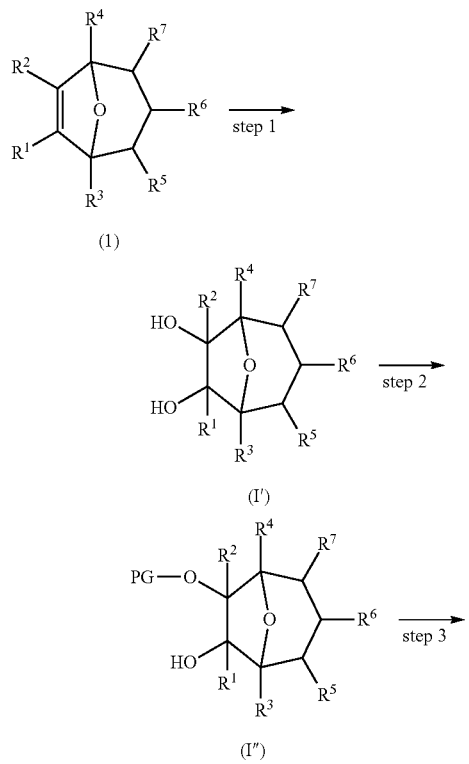

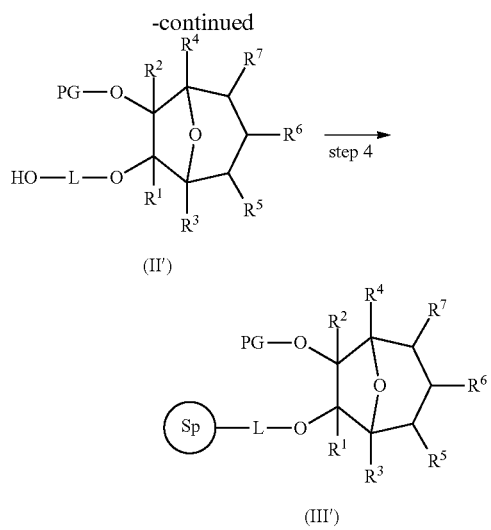

wherein PG is a hydroxy-protecting group which is cleaved with an acid; and other symbols are as defined above.

1. Step 1

In step 1 of the above-mentioned scheme, compound (1) is reacted in a solvent in the presence of osmium tetraoxide and a reoxidant to give compound (I'). Examples of the solvent include halogenated solvents (e.g., chloroform, dichloromethane, 1,2-dichloroethane etc.), aromatic solvents (e.g., benzene, toluene, xylene, mesitylene etc.), aliphatic solvents (e.g., hexane, pentane, heptane, octane, nonane, cyclohexane etc.), ether solvents (e.g., diethyl ether, cyclopentyl methyl ether, tert-butyl methyl ether, tetrahydrofuran etc.), amide solvents (e.g., N,N-dimethylformamide etc.), alcohol solvent (e.g., tert-butanol etc.), water and the like, and a mixture of two or more kinds thereof may be used. Examples of the reoxidant include N-methylmorpholine N-oxide, trimethylamine N-oxide, tert-butyl hydroperoxide and the like.

2. Step 2

In step 2 of the above-mentioned scheme, compound (I') is reacted with a protecting agent under basic conditions to give compound (I''). Examples of the base include organic base (e.g., pyridine, triethylamine etc.), inorganic base (e.g., sodium carbonate etc.) and the like is not particularly limited. The protecting agent is not particularly limited as long as it is a reagent generally used for introducing "a hydroxy-protecting group which is cleaved with an acid" in the organic synthesis, and examples thereof include halogenated trityls (e.g., 4,4'-dimethoxytrityl chloride etc.), halogenated silyls (e.g., trimethylsilyl chloride etc.) and the like. Where necessary, a solvent may be used. The solvent only needs to be an inert solvent, and those similar to the solvents recited in step 1 can be used.

3. Step 3

In step 3 of the above-mentioned scheme, a group represented by HO-L- is introduced into compound (I'') to give compound (II'). Examples of the introduction method include a method for reacting with a corresponding acid anhydride. The acid anhydride only needs to correspond to the group to be introduced, and examples thereof include succinic anhydride, glutaric anhydride and the like. Where necessary, a base and an activating agent may also be added. As the base, those similar to the bases recited in step 2 can be used. Examples of the activating agent include N,N-dimethyl-4-aminopyridine (DMAP) and the like. Where necessary, a solvent may be used. The solvent only needs to be an inert solvent, and those similar to the solvents recited in step 1 can be used.

4. Step 4

In step 4 of the above-mentioned scheme, compound (II') is reacted with a solid phase support in a solvent in the presence of a condensing agent and a base to give a support for solid phase synthesis of nucleic acid (III'). Examples of the solvent include halogenated solvents (e.g., chloroform, dichloromethane, 1,2-dichloroethane etc.), aromatic solvents (e.g., benzene, toluene, xylene, mesitylene etc.), aliphatic solvents (e.g., hexane, pentane, heptane, octane, nonane, cyclohexane etc.), ether solvents (e.g., diethyl ether, cyclopentyl methyl ether, tert-butyl methyl ether, tetrahydrofuran etc.), amide solvents (e.g., N,N-dimethylformamide etc.), nitrile solvents (e.g., acetonitrile etc.)) and the like. A mixture of two or more kinds thereof may be used. Examples of the condensing agent include O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), N-ethyl-N'-3-dimethylaminopropylcarbodiimide (EDC) and hydrochlorides thereof and the like. Examples of the base include N,N-diisopropylethylamine, triethylamine, pyridine, 4-dimethylaminopyridine, N-methylimidazole and the like.

The obtained support (III') for solid phase synthesis of nucleic acid may be subjected to a capping treatment where necessary by a known method. For example, an unreacted carboxy group can be capped by esterification with alcohols such as methanol, ethanol and the like in the aforementioned solvent in the presence of the aforementioned condensing agent and the aforementioned base. The unreacted —OH group or —NH$_2$ group can be capped by reacting with acetic anhydride in the aforementioned solvent in the presence of the aforementioned base, to allow for acetylation.

In each of steps 1-4, the reaction temperature and the reaction time can be appropriately set according to the reagent to be used, concentration conditions, reaction rate and the like. For example, the reaction temperature is generally −80° C. to 150° C., and the reaction time is generally 0.1 hr to 200 hr. The amount of each reagent can be appropriately set according to each reaction. For example, it is 0.01 mol equivalent excess amount, relative to the reactant. The material compound may be in a salt form.

For nucleic acid synthesis using the support for solid phase synthesis of nucleic acid of the present invention, a nucleic acid automatic synthesizer is used and various synthesis methods known per se can be used. In the present specification, the "nucleic acid synthesis reaction" particularly means an elongation reaction of nucleotide constituting a nucleic acid. Hence, nucleotides are sequentially bound to a nucleoside, nucleotide or oligonucleotide bound to the solid phase support, whereby an elongated oligonucleotide is obtained.

The nucleic acid synthesis reaction can be performed by the H-phosphonate method, phosphoester method, solid phase phosphoramidite method and the like. Of these, since high capacity of synthesizing nucleic acid and high purity of nucleic acid are obtained, a solid phase phosphoramidite method is preferable.

A preferable embodiment of the nucleic acid synthesis reaction by a solid phase phosphoramidite method includes, for example, a method including placing the support (III') for solid phase synthesis of nucleic acid of the present invention in a reaction column of a nucleic acid automatic synthesizer, performing steps A1-A3 shown below, further repeating steps B1-B3 a single time or plural times, and finally performing step C2 (step C1 where necessary) to produce nucleic acid.

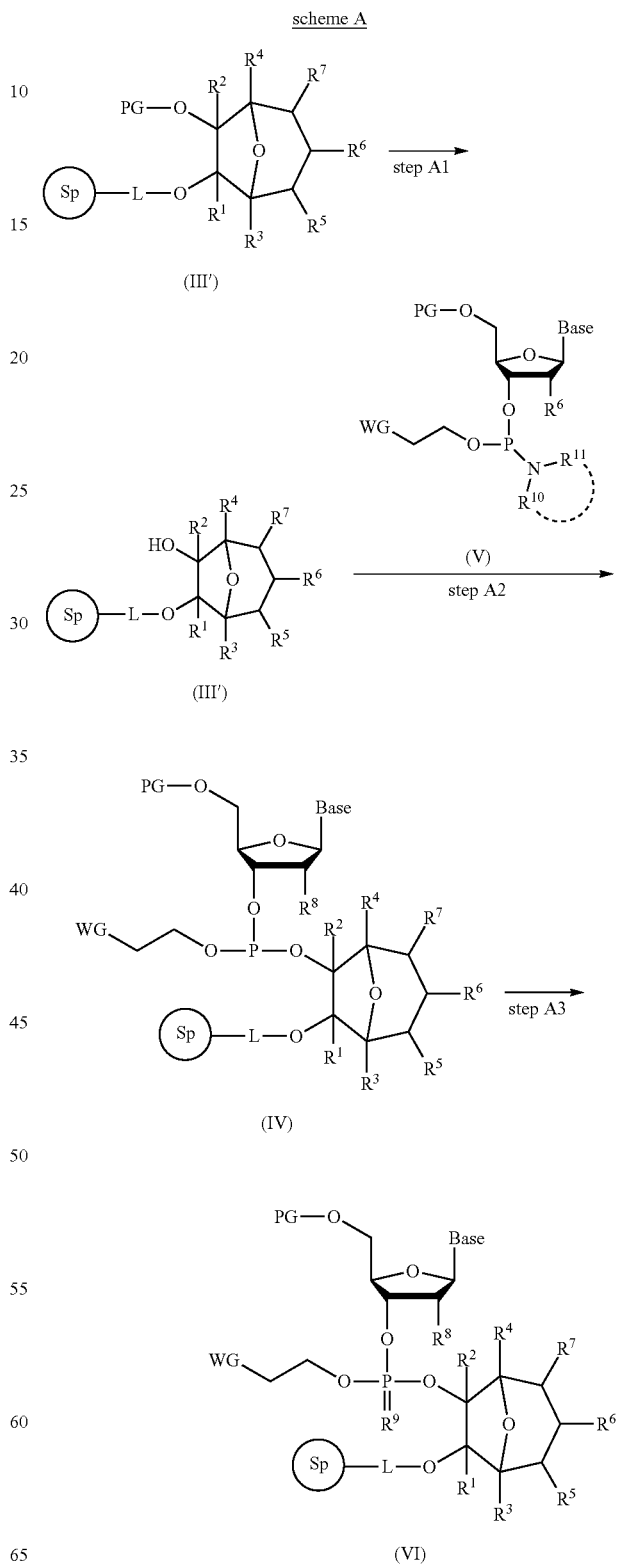

scheme A scheme B
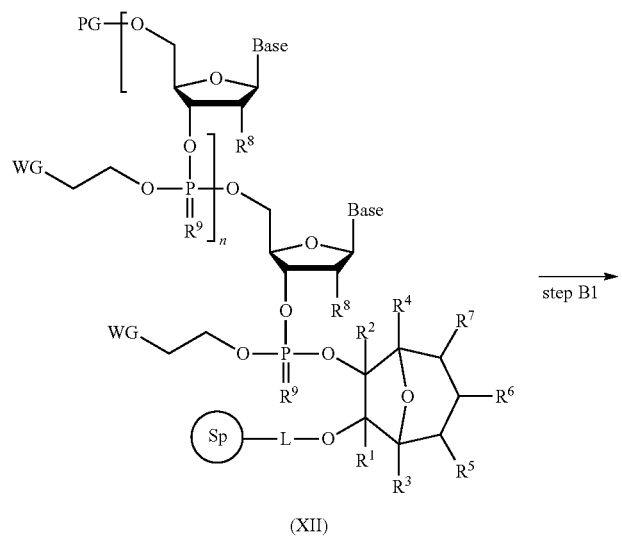
(XII)
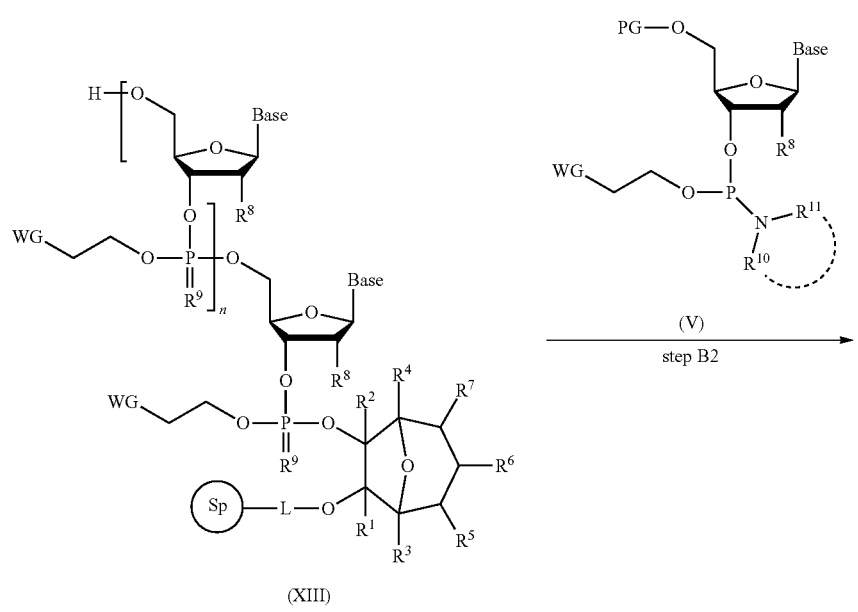
(XIII)

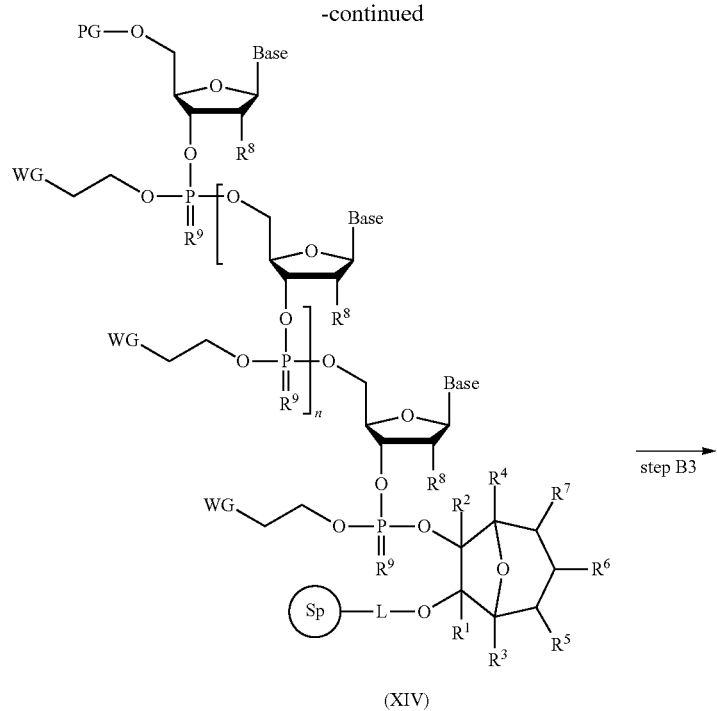
(XIV)
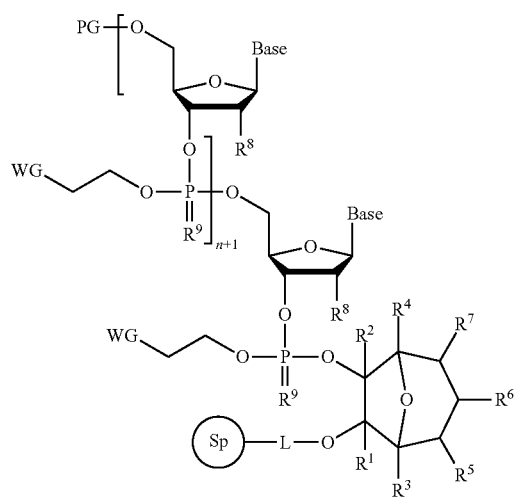
(XVI)

scheme C

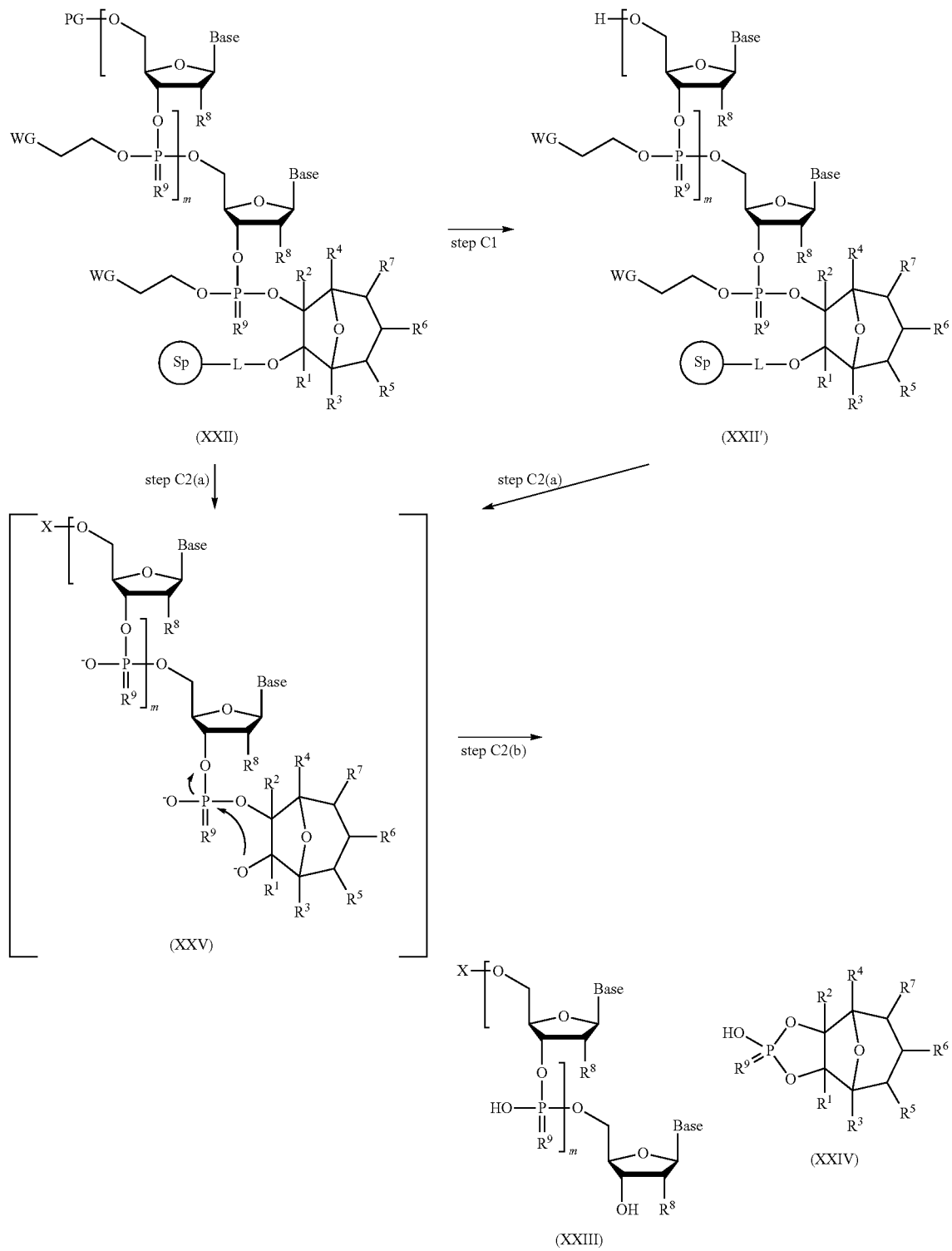

wherein each Base independently shows an optionally protected nucleic acid base; each WG independently shows an electron-withdrawing group; each $R^8$ is independently a hydrogen atom or optionally protected hydroxy group; each $R^9$ is independently O or S; $R^{10}$ and $R^{11}$ are each independently a $C_{1-6}$ alkyl group or optionally joined to form a ring; n is an integer of not less than 0; m is an integer of one or more; and other symbols are as defined above.

In the present specification, the "nucleic acid base" is not particularly limited as long as it is used for the synthesis of nucleic acid and examples thereof include cytosinyl group, uracil group, thyminyl group, adenyl group, guanylyl group, and modified nucleic acid bases thereof (e.g., 8-bromoadenyl group, 8-bromoguanylyl group, 5-bromocytosinyl group, 5-iodocytosinyl group, 5-bromouracil group, 5-iodouracil group, 5-fluorouracil group, 5-methylcytosinyl group, 8-oxoguanylyl group, hypoxanthinyl group and the like).

In the present specification, the "optionally protected nucleic acid base" means, for example, that adenyl group, guanylyl group and cytosinyl group or amino group of modified nucleic acid base may be protected. The amino-protecting group is not particularly limited as long as it is used as a protecting group of a nucleic acid. Specific examples thereof include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and the like.

Examples of the "electron-withdrawing group" for WG include cyano, nitro, $C_{1-6}$ alkylsulfonyl, and a halogen atom, and cyano is preferable.

Examples of the "optionally protected hydroxy group" for $R^8$ include hydroxy groups optionally protected by 2-cyanoethyl, 2-nitroethyl, 4-nitrophenethyl, phenylsulfonylethyl, methylsulfonylethyl, trimethylsilylethyl, diphenylcarbamoyl, dimethylcarbamoyl, diethylcarbamoyl, methylphenylcarbamoyl, 1-pyrrolidinylcarbamoyl, morpholinocarbamoyl, 4-(tert-butylcarboxy)benzyl, 4-[(dimethylamino)carboxy]benzyl, 4-(phenylcarboxy)benzyl, and silyl protecting group and the like.

n is preferably an integer of 0-200, more preferably, an integer of 1-100; m is preferably an integer of 1-201, more preferably, an integer of 2-101.

1. Deprotection Step (Steps A1, B1 and C1)

In the above-mentioned scheme, the deprotection step shown by steps A1, B1 and C1 includes flowing an acid through a reaction column and removing the hydroxy-protecting group in support (III'), (XII) or (XXII). Examples of the acid include trifluoroacetic acid, dichloroacetic acid, trifluoromethanesulfonic acid, trichloroacetic acid, methanesulfonic acid, hydrochloric acid, acetic acid, p-toluenesulfonic acid and the like. The acid may be used alone or mixed with a solvent. Examples of the solvent include halogenated solvents (e.g., chloroform, dichloromethane, 1,2-dichloroethane etc.), aromatic solvents (e.g., benzene, toluene, xylene, mesitylene etc.), aliphatic solvents (e.g., hexane, pentane, heptane, octane, nonane, cyclohexane etc.), ether solvents (e.g., diethyl ether, cyclopentyl methyl ether, tert-butyl methyl ether, tetrahydrofuran etc.) and the like. Two or more kinds of these solvents may be used in a mixture in an appropriate ratio. Lastly in this step, washing with the above-mentioned solvent is desirably performed.

2. Condensation Step (Steps A2 and B2)

In the above-mentioned scheme, the condensation step shown by steps A2 and B2 includes a condensation reaction of phosphoramidite (V) and hydroxy group of support (III") or (XIII) in a solvent. Examples of the solvent include those similar to the solvents used in the deprotection step. In this step, an activating agent may be used as necessary. Examples of the activating agent include, but are not limited to, 1H-tetrazole, 4,5-dicyanoimidazole, 5-ethylthio-1H-tetrazole, benzimidazolium triflate (BIT), N-phenylbenzimidazolium triflate, imidazolium triflate (IMT), N-PhIMP, 5-nitrobenzimidazolium triflate, triazolium triflate, 1-hydroxybenzotriazole (HOBT), N-(cyanomethyl)pyrrolidinium tetrafluoroborate and the like. After the above-mentioned reaction, unreacted hydroxy group may be capped as necessary by a known method such as acetylation by an acetic anhydride treatment and the like. Lastly in this step, washing with the above-mentioned solvent is desirably performed.

3. Oxidation or Sulfuration Step (Steps A3 and B3)

In the above-mentioned scheme, the oxidation or sulfuration step shown by steps A3 and B3 includes oxidation or sulfuration of support (IV) or (XIV) by reacting with an oxidant or sulfurizing agent in a solvent. Examples of the solvent include those similar to the solvents used in the deprotection step. Examples of the oxidant include iodine, m-chloroperbenzoic acid, tert-butyl hydroperoxide, 2-butanone peroxide, bis(trimethylsilyl) peroxide, 1,1-dihydroperoxycyclododecane, hydrogen peroxide and the like. Examples of the sulfurizing agent include 3-((N,N-dimethylaminomethylidene)amino)-3H-1,2,4-dithiazole-5-thione, 3H-1,2-benzodithiol-3-one-1,1-dioxide, 3H-1,2-benzodithiol-3-one, phenylacetyl disulfide, tetraethylthiuram disulfide, 3-amino-1,2,4-dithiazole-5-thione, sulfur and the like. Lastly in this step, washing with the above-mentioned solvent is desirably performed.

4. Post-Treatment Step (Step C2)

In the above-mentioned scheme, the post-treatment step shown by step C2 includes treating support (XXII) or (XXII') with ammonia and/or amines to recover nucleic acid (XXIII). Examples of amine include methylamine, ethylamine, isopropylamine, ethylenediamine, diethylamine, triethylamine and the like. Ammonia and/or amines are desirably used in a mixture with a solvent. Examples of the solvent include water, alcohols (e.g., methanol, ethanol etc.) and the like. Two or more kinds of these solvents may be used in a mixture in an appropriate ratio. By this step, nucleic acid (XXIII) having a hydroxy group at the 3'-terminal is produced via intermediate (XXV).

EXAMPLES

The present invention is explained in more detail in the following by referring to Examples, which are not to be construed as limitative.

Synthetic Example 1

Compound (d) was synthesized according to the following synthesis scheme (synthesis was committed to Shinsei Chemical Company Ltd.).

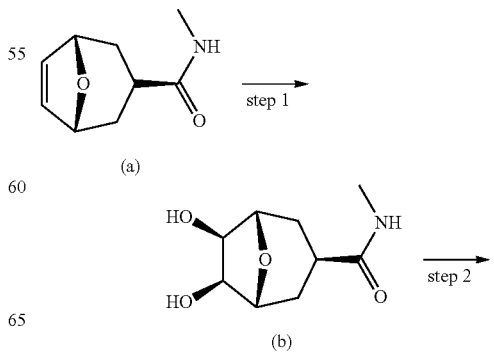

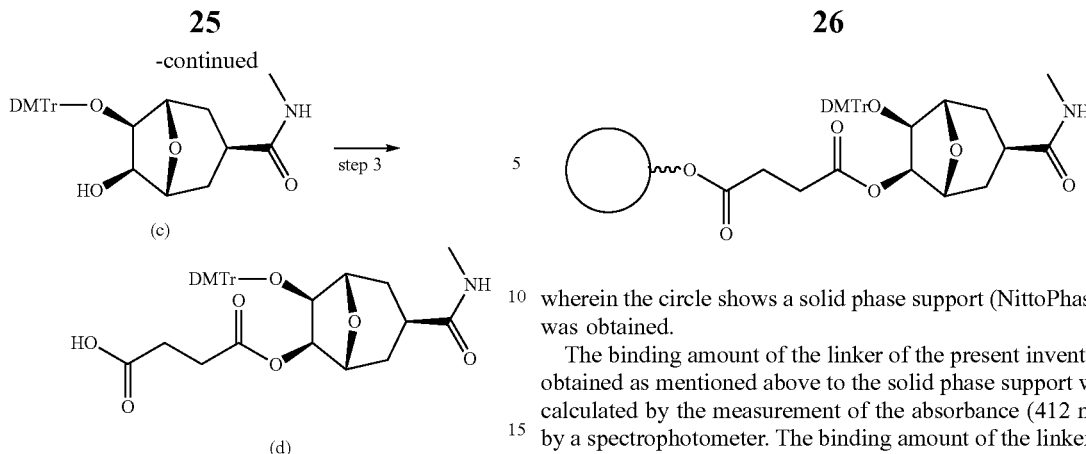

wherein DMTr shows a 4,4'-dimethoxytrityl group.

(step 1) Compound (a) obtained by a method similar to the method described in WO 2001/034604 was dissolved in a tert-butanol (t-BuOH)/water mixture, and 2 equivalents of N-methylmorpholine N-oxide was added. Osmium tetraoxide (t-BuOH) (0.1 equivalent) was added, and the mixture was stirred at room temperature overnight. After completion of the reaction, the reaction was quenched by adding aqueous $Na_2SO_3$ solution and purified by silica gel column to give compound (b).

(step 2) Compound (b) was dissolved in pyridine, and cooled to −20° C. DMTr-Cl (1.5 equivalents) was added, and the mixture was stirred at room temperature overnight, concentrated, and purified by silica gel column to give compound (c).

(step 3) Compound (c) was dissolved in pyridine, 5 equivalents of succinic anhydride and a catalytic amount of DMAP were added and the mixture was stirred for 2 days, concentrated, purified by silica gel column and dispensed by HPLC to give compound (d).

Example 1

Synthesis of DNA 20 mer (DMT-on) by Using Support (A) for Solid Phase Synthesis of Nucleic Acid Compound (d) (0.018 g) obtained by the method shown in Synthetic Example 1 and a porous polystyrene solid phase support having a hydroxyl group (NittoPhase (registered trade mark), manufactured by NITTO DENKO Co., Ltd.) (0.5 g) were dispersed in acetonitrile (5 mL), and HBTU (0.014 g) and N,N-diisopropylethylamine (0.013 mL) were added. The mixture was reacted at 28° C. for 23 hr to carry the aforementioned compound on the solid phase support. The solid phase support was washed with acetonitrile (250 mL), and acetic anhydride (0.25 mL), N-methylimidazole (0.25 mL), pyridine (0.38 mL), 4-dimethylaminopyridine (0.0125 g), acetonitrile (4.13 mL) were added, and the mixture was reacted at 28° C. for 22 hr to cap the unreacted hydroxy group and washed with acetonitrile (250 mL), whereby support (A) for solid phase synthesis of nucleic acid, which is represented by the following formula:

wherein the circle shows a solid phase support (NittoPhase), was obtained.

The binding amount of the linker of the present invention obtained as mentioned above to the solid phase support was calculated by the measurement of the absorbance (412 nm) by a spectrophotometer. The binding amount of the linker to the solid phase support was 52.7 μmol/g.

Support (A) for solid phase synthesis of nucleic acid (19.0 mg) was filled in a reaction column, and DNA oligonucleotide of 20 mer (5'-ATACCGATTAAGCGAAGTTT-3': SEQ ID NO: 1) was synthesized with DMT-on (method without removing 5'-terminal protecting group) (synthesis scale 1 μmol) by using nucleic acid synthesizer nS-8 II (manufactured by GeneDesign, Inc.). After the synthesis, the solid phase support with the DNA oligonucleotide bonded thereto was immersed in a 30% aqueous ammonia/ethanol (3:1) mixed solution at 55° C. for 15 hr to cut out the DNA oligonucleotide from the solid phase support.

Comparative Example 1

Synthesis of DNA 20 mer (DMT-on) by Using DMT-dT-3'-Succinate-Bound Support for Solid Phase Synthesis of Nucleic Acid In the same manner as in Example 1, a cleavable linker DMT-dT-3'-succinate (manufactured by Beijing OM Chemicals) was bonded to commercially available solid phase support NittoPhase (registered trade mark) (manufactured by NITTO DENKO CORPORATION). The binding amount of the compound to the solid phase support was measured by a method similar to that of Example 1. As a result, the binding amount was 59.7 μmol/g.

The solid phase support (16.8 mg) was filled in a reaction column and, in the same manner as in Example 1, DNA oligonucleotide of 20 mer (5'-ATACCGATTAAGC-GAAGTTT-3': SEQ ID NO: 1) was synthesized with DMT-on (method without removing 5'-terminal protecting group) (synthesis scale 1 μmol). After the synthesis, the DNA oligonucleotide was cut out from the solid phase support.

Experimental Example 1

The DNA oligonucleotide solutions obtained in Example 1 and Comparative Example 1 were measured by high performance liquid chromatography (HPLC) (measurement conditions: column; Waters XBridge OST C18 2.5 μm 50×4.6 mm, UV detection; 260 nm, Buffer A; 100 mM HFIP/7 mM TEA in Water, pH 8.0, Buffer B; methanol, temperature; 30° C.). FIG. 1(a) and FIG. 1(b) show each HPLC chart.

In addition, the DNA oligonucleotide solutions obtained in Example 1 and Comparative Example 1 were subjected to LC-MS analysis (measurement conditions: column; Waters XBridge OST C18 2.5 μm 50×4.6 mm, UV detection; 254 nm, Buffer A; HFIP/7 mM TEA in Water, pH 8.0, Buffer B; methanol, temperature; 30° C.)

As a result, the main peak of the DNA oligonucleotide prepared in Example 1 was confirmed to be that of a DNA oligonucleotide (20 mer) having a hydroxy group at the 3'-terminal (molecular weight (measured value); 6439). On the other hand, the main peak of the DNA oligonucleotide prepared in Comparative Example 1 was confirmed to be that of a DNA oligonucleotide (20 mer) having a hydroxy group at the 3'-terminal (molecular weight (measured value); 6439).

Example 2

Synthesis of RNA 21 mer (DMT-off) by Using Support (A) for Solid Phase Synthesis of Nucleic Acid Support (A) for solid phase synthesis of nucleic acid was obtained in the same manner as in Example 1 from compound (d) (0.018 g) obtained by the method shown in Synthetic Example 1.

Support (A) for solid phase synthesis of nucleic acid 15.8 mg was filled in a reaction column, and RNA oligonucleotide of 21 mer (5'r(CGAGAAGCGCGAUACCAUGU)dT3':SEQ ID NO: 2) was synthesized with DMT-off (method removing 5'-terminal protecting group) by using DNA/RNA automatic synthesizer ABI3400 (manufactured by Applied Biosystems) (synthesis scale 1 μmol). After the synthesis, the solid phase support with the RNA oligonucleotide bonded thereto was immersed in a 30% aqueous ammonia/methylamine (1:1) mixed solution at 65° C. for 1.5 hr to cut out the RNA oligonucleotide from the solid phase support. Thereafter, triethylamine trihydrogen fluoride/dimethyl sulfoxide (5:1) was added, and the mixture was incubated at 65° C. for 1.5 hr. RNA 2'-terminal protecting group and tert-butyldimethylsilyl (TBDMS) group were removed, and 50 μM sodium acetate solution was added.

Comparative Example 2

Synthesis of RNA 21 mer (DMT-off) by Using Support (B) for Solid Phase Synthesis of Nucleic Acid Ethylene and furan were added into a Schlenk reaction tube, and reacted at room temperature. Using osmium tetraoxide as a catalyst, the resultant product was oxidized. Then, 4,4'-dimethoxytrityl chloride was reacted, and a part of the hydroxy group was protected with a DMTr group to give a compound. Thereafter, a porous polystyrene solid phase support having a hydroxyl group (NittoPhase (registered trade mark), manufactured by NITTO DENKO Co., Ltd.) and introduced with a succinyl group was dispersed in acetonitrile, and the aforementioned compound, HBTU and N,N-diisopropylethylamine were added. The mixture was reacted at 28° C. for 23 hr to carry the aforementioned compound on the solid phase support. Acetic anhydride, N-methylimidazole, pyridine, 4-dimethylaminopyridine, and acetonitrile were added, and the mixture was reacted at 28° C. for 22 hr to cap the unreacted hydroxy group, whereby support (B) for solid phase synthesis of nucleic acid, which is represented by the following formula:

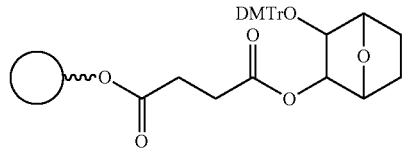

was obtained.

The binding amount of the linker obtained as mentioned above to the solid phase support was measured by a method similar to that of Example 1. As a result, the binding amount was 36.8 μmol/g.

Support (B) for solid phase synthesis of nucleic acid (27.1 mg) was filled in a reaction column and, in the same manner as in Example 2, RNA oligonucleotide of 21 mer (5'r (CGAGAAGCGCGAUACCAUGU)dT3':SEQ ID NO: 2) was synthesized with DMT-off (method removing 5'-terminal protecting group) (synthesis scale 1 μmol). After the synthesis, the RNA oligonucleotide was cut out from the support for solid phase synthesis of nucleic acid. Thereafter, RNA 2'-terminal protecting group, TBDMS group, was removed.

Experimental Example 2

The RNA oligonucleotide solutions obtained in Example 2 and Comparative Example 2 were measured by high performance liquid chromatography (HPLC) (measurement condition: column; Waters XBridge OST C18 2.5 μm 50×4.6 mm, UV detection; 260 nm, Buffer A; 100 mM HFIP/7 mM TEA in Water, pH 8.0, Buffer B; methanol, temperature; 60° C.). FIG. 2(a) and FIG. 2(b) show each HPLC chart.

In addition, the RNA oligonucleotide solutions obtained in Example 2 and Comparative Example 2 were subjected to LC-MS analysis (measurement conditions: column; Waters XBridge OST C18 2.5 μm 50×4.6 mm, UV detection; 254 nm, Buffer A; HFIP/7 mM TEA in Water, pH 8.0, Buffer B; methanol, temperature; 60° C.)

As a result, the RNA oligonucleotide prepared in Example 2 has two main peaks, and the earlier big peak was confirmed to be that of an RNA oligonucleotide (21 mer) having a hydroxy group at the 3'-terminal (molecular weight (measured value); 7036), and the later small peak was confirmed to be that of impurity. On the other hand, the RNA oligonucleotide prepared in Comparative Example 2 has two main peaks, and one of them was confirmed to be that of an RNA oligonucleotide (21 mer) having a hydroxy group at the 3'-terminal and the other was confirmed to be that of RNA 21 mer bound with a linker (impurity) (molecular weight (measured value); 7219).

Figure 2:
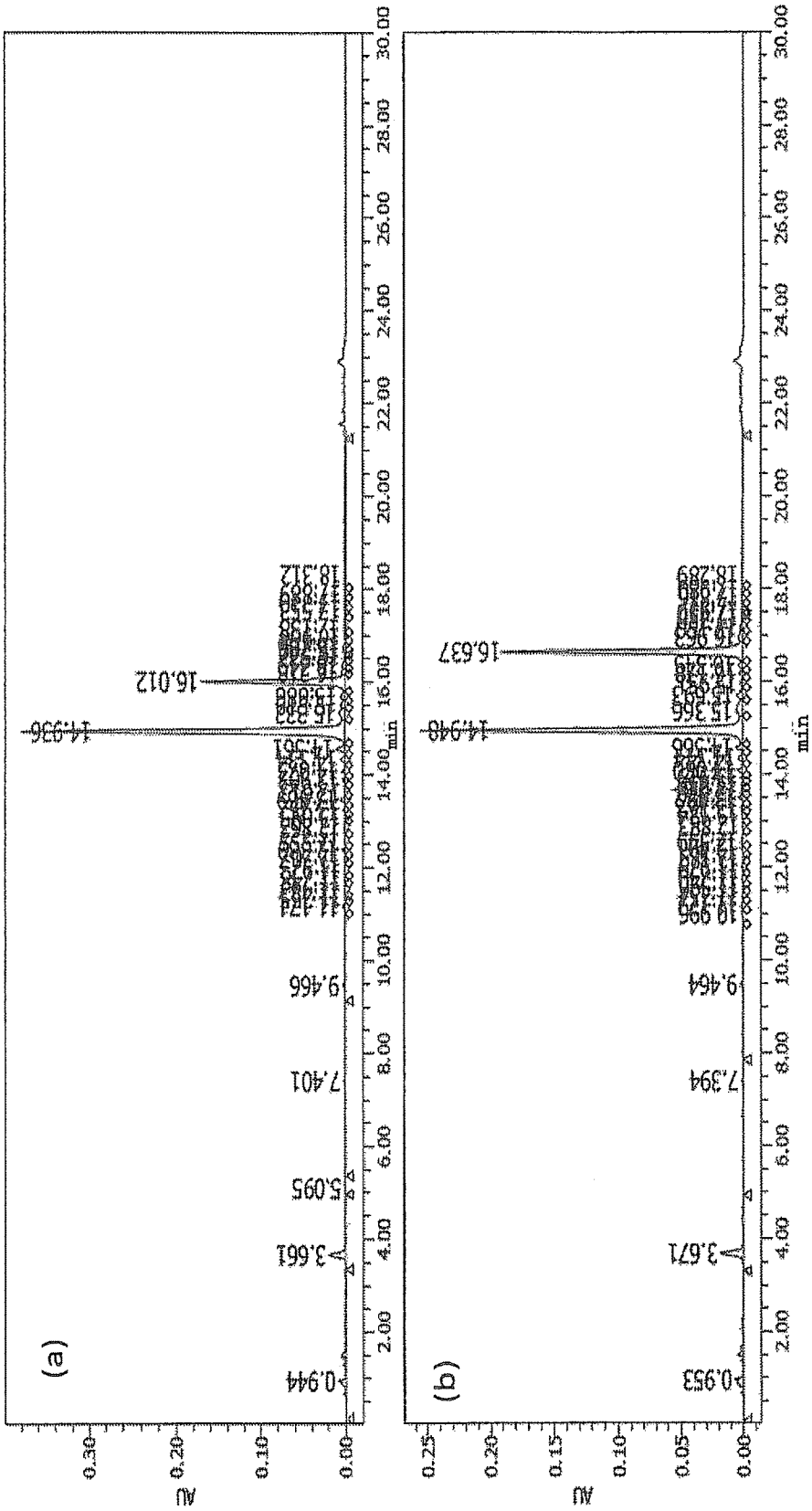
FIG. 2 shows HPLC charts of the RNA oligonucleotide solutions obtained in Example 2 (FIG. 2(a)) and Comparative Example 2 (FIG. 2(b)).

As shown in FIG. 2, the RNA oligonucleotide prepared in Example 2 showed a smaller ratio of impurity peak as compared to that in Comparative Example 2, and was found to suppress generation of impurity. Thus, it was shown that support (A) for solid phase synthesis of nucleic acid of the present invention, which has a bridged ring structure constituted of 7 carbon atoms and one oxygen atom, has higher properties as a universal support, as compared to support (B) for solid phase synthesis of nucleic acid, which has a bridged ring structure constituted of 6 carbon atoms and one oxygen atom.

Table 1 collectively show the data obtained in Experimental Examples 1 and 2.

TABLE 1

|  |  | solid phase support | sequence | molecular weight |
|---|---|---|---|---|
| Experimental Example 1 | Example 1 | (A) | DNA 20 mer (SEQ ID NO: 1) DMT-on | 6439 |
|  | Comparative Example 1 | DMT-dT-3'-Succinate |  | 6439 |
| Experimental Example 2 | Example 2 | (A) | RNA 21 mer (SEQ ID NO: 2) DMT-off + linker | 7036 |
|  | Comparative Example 2 | (B) |  | 7036 7219 |

INDUSTRIAL APPLICABILITY

Since the support for solid phase synthesis of nucleic acid of the present invention can inhibit generation of byproducts and can synthesize DNA or RNA more efficiently at a high purity, it can be used widely for the production and development of various nucleic acid drugs.

This application is based on a patent application No. 2015-089197 filed in Japan, the contents of which are incorporated in full herein.

The invention claimed is:

1. A linker for solid phase synthesis of nucleic acid, consisting of a compound represented by the formula (I):

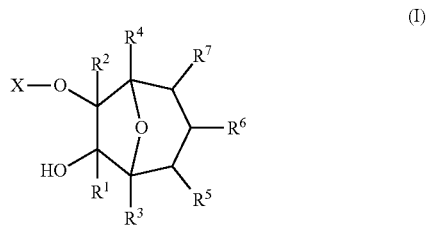

wherein

X is a trityl protecting group or a silyl protecting group; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by a cyano group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

2. A linker for solid phase synthesis of nucleic acid, consisting of a compound represented by the formula (II):

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Artificial Synthetic oligonucleotide (20mer)

<400> SEQUENCE: 1
ataccgatta agcgaagttt                                              20

<210> SEQ ID NO 2
<211> LENGTH: 21
<212> TYPE: RNA
<213> ORGANISM: Artificial Sequence
<220> FEATURE:
<223> OTHER INFORMATION: Artificial Synthetic oligonucleotide (21mer)
<220> FEATURE:
<223> OTHER INFORMATION: Combined DNA/RNA
<220> FEATURE:
<221> NAME/KEY: misc_feature
<222> LOCATION: (21)..(21)
<223> OTHER INFORMATION: n is deoxythymidine

<400> SEQUENCE: 2
cgagaagcgc gauaccaugu n                                            21
```

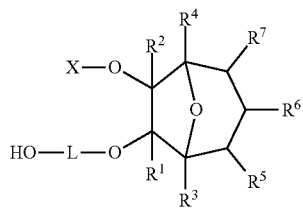

(II)

wherein

X is a hydrogen atom, a trityl protecting group, or a silyl protecting group;

L is a divalent group of formula (L):

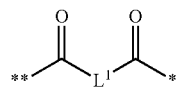

(L)

wherein $L^1$ is an inactive divalent group; and * and ** each denote a binding site; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by a cyano group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

3. A support for solid phase synthesis of nucleic acid, having a structure shown by the formula (III):

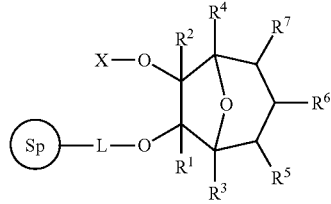

(III)

wherein

X is a hydrogen atom, a trityl protecting group, or a silyl protecting group;

L is a divalent group of formula (L):

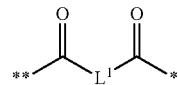

(L)

wherein $L^1$ is an inactive divalent group; and * and ** each denote a binding site;

Sp is a solid phase support; and $R^1$-$R^7$ are each independently (1) a hydrogen atom; (2) a cyano group; (3) a nitro group; (4) a carbamoyl group optionally mono- or di-substituted by substituent(s) selected from a $C_{1-6}$ alkyl group and a phenyl group; (5) a $C_{1-6}$ alkyl group optionally substituted by a $C_{1-6}$ alkoxy group; (6) a phenyl group optionally substituted by substituent(s) selected from a $C_{1-6}$ alkoxy group, a $C_{1-6}$ alkyl group, a nitro group, and a halogen atom; (7) a $C_{1-6}$ alkoxy group optionally substituted by a cyano group; (8) a phenoxy group; (9) a $C_{1-7}$ acyl group; (10) a mono- or di-$C_{1-6}$ alkylamino group; (11) a mono- or di-phenylamino group; (12) a $C_{1-7}$ acylamino group; or (13) a halogen atom.

4. The support for solid phase synthesis of nucleic acid according to claim 3, wherein X is a trityl protecting group or a silyl protecting group.

5. The support for solid phase synthesis of nucleic acid according to claim 3, wherein the bond between Sp and L is an amide bond or an ester bond.

6. The support for solid phase synthesis of nucleic acid according to claim 3, wherein Sp is a solid phase support of a porous polymer support or a porous glass support.

7. A method of producing a nucleic acid, comprising a step of performing a nucleic acid synthesis reaction on the support for solid phase synthesis of nucleic acid according to claim 3.

8. The production method according to claim 7, wherein the nucleic acid synthesis reaction is performed by a solid phase phosphoramidite method.

9. The linker for solid phase synthesis of nucleic acid according to claim 2, wherein X is a trityl protecting group or a silyl protecting group.

10. The linker for solid phase synthesis of nucleic acid according to claim 1, wherein X is a trityl protecting group, $R^1$-$R^5$ and $R^7$ are hydrogen atoms, and $R^6$ is a carbamoyl group optionally mono- or di-substituted by substituent(s) selected from $C_{1-6}$ alkyl group and phenyl group.

11. The linker for solid phase synthesis of nucleic acid according to claim 2, wherein X is a trityl protecting group, $R^1$-$R^5$ and $R^7$ are hydrogen atoms, and $R^6$ is a carbamoyl group optionally mono- or di-substituted by substituent(s) selected from $C_{1-6}$ alkyl group and phenyl group.

* * * * *